United States Patent [19]
Cooper

[11] Patent Number: 5,770,374
[45] Date of Patent: Jun. 23, 1998

[54] METHODS FOR IDENTIFYING ONCOGENES AND ANTI-ONCOGENES

[75] Inventor: Mark J. Cooper, Solon, Ohio

[73] Assignee: Case Western Reserve University, Cleveland, Ohio

[21] Appl. No.: 728,608

[22] Filed: Oct. 10, 1996

Related U.S. Application Data

[63] Continuation of Ser. No. 479,204, Jun. 7, 1995, and a continuation of Ser. No. 594,299, Jan. 30, 1996, which is a continuation of Ser. No. 151,387, Nov. 12, 1993, abandoned, said Ser. No. 479,204, is a continuation of Ser. No. 151,387.

[51] Int. Cl.$^6$ .................................................... C12Q 1/68
[52] U.S. Cl. ............................................................... 435/6
[58] Field of Search ................................. 435/6, 320.1, 5

[56] References Cited

PUBLICATIONS

Hambor, et al., "Use of an Epstein–Barr Virus Episomal Replicon for Anti–Sense RNA–Mediated Gene Inhibition in a Human Cytotoxic T–Cell Clone", 1988, *Proc. Natl. Acad. Sci., U.S.A.,* 85:4010–4014.

Subramanian, et al., "Nucleotide Sequence of a Fragment of SV40 DNA That Contains the Origin of DNA Replication and Specifies the 5' Ends of 'Early' and 'Late' Viral RNA", 1977, *J. Biol. Chem.,* 252:355–367.

Lin, et al., "Stable T–p53 Complexes Are Not Required for Replication of Simian Virus 40 in Culture or for Enhanced Phosphorylation of T Antigen and p53", 1991, *J. Virol.,* 65:2066–2072.

Lin, et al., "The Ability of Large T Antigen To Complex with p53 Is Necessary for the Increased Life Span and Partial Transformation of Human Cells by Simian Virus 40", 1991, *J. Virol.,* 65:6447–6453.

Deyerle, et al., "Analysis of Origin of DNA Replication of Human Papovavirus BK", 1989, *J. Virol.,* 63:356–365.

Reddy, et al., "The Genome of Simian Virus 40", 1978, *Science,* 200:494–502.

Felgner, et al., "Lipofection: A Highly Efficient, Lipid–Mediated DNA–Transfection Procedure", 1987, *Proc. Natl. Acad. Sci., U.S.A.,* 84:7413–7417.

Fiers, et al., "Complete Nucleotide Sequence of SV40 DNA", 1978, *Nature,* 273:113–120.

Van Heuverswyn, et al., "Nucleotide Sequence of the Hind–C Fragment of Simian Virus 40 DNA", 1979, *Eur. J. Biochem.,* 100:51–60.

Roberts, et al., "Negative Control of DNA Replication in Composite SV40–Bovine Papilloma Virus Plasmids", 1986, *Cell,* 46:741–752.

Ryder, et al., "Binding of SV40 A Protein to the BK Virus Origin of DNA Replication", 1983, *Virology,* 129:239–245.

Hanahan, D., "Transgenic Mice as Probes into Complex Systems", 1989, *Science,* 246:1265–1275.

Michalovitz, et al., "Activated Ha–ras Can Cooperate with Defective Simian Virus 40 in the Transformation of Non-established Rat Embryo Fibroblasts", 1987, *J. Virol.,* 61:2648–2654.

Shin, et al., "Tumorigenicity of Virus–Transformed Cells in Nude Mice is Correlated Specifically with Anchorage Independent Growth In Vitro", 1975, *Proc. Natl. Acad. Sci., U.S.A.,* 72:4435–4439.

Christian, et al., "Characterization of Human Uroepithelial Cells Immortalized In Vitro by Simian Virus 40$^1$", 1987, *Cancer Res.,* 47:6066–6073.

Sarver, et al., "Bovine Papilloma Virus Deoxyribonucleic Acid: a Novel Eucaryotic Cloning Vector", 1981, *Mol. & Cell. Biol.,* 1:486–496.

Tsui, et al., "Persistence of Freely Replicating SV40 Recombinant Molecules Carrying a Selectable Marker in Permissive Simian Cells", 1982, *Cell,* 30:499–508.

Belt, et al., "Construction and Properties of an Epstein–Barr-r–Virus–Derived cDNA Expression Vector for Human Cells", 1989, *Gene,* 84:407–417.

Yates, et al., "Stable replication of plasmids derived from Epstein–Barr Virus in Various Mammalian Cells", 1985, *Nature,* 313:812–815.

Cherington, et al., "Separation of Simian Virus 40 Large–T–Antigen–Transforming and Origin–Binding Functions from the Ability to Block Differentiation", 1988, *Mol. & Cell. Biol.,,* 8:1380–1384.

Chittenden, et al., "Functional Limits of oriP, the Epstein–Barr Virus Plasmid Origin of Replication", 1989, *J. Virol.,* 63:3016–3025.

Milanesi, et al., "BK Virus–Plasmid Expression Vector That Persists Episomally in Human Cells and Shuttles into *Escherichia coli*", 1984, *Mol. & Cell. Biol.,* 4:1551–1560.

Vidal, et al., "Differences in Human Cell Lines to Support Stable Replication of Epstein–Barr Virus–Based Vectors", 1990, *Biochim. Biophys. Acta,* 1048:171–177.

Yates, et al., "A Cis–Acting Element from the Epstein–Barr Viral Genome That Permits Stable Replication of Recombinant Plasmids in Latently Infected Cells", 1984, *Proc. Natl. Acad. Sci.,U.S.A.,* 81:3806–3810.

Lutfalla, et al., "Construction of an EBNA–Producing Line of Well–Differentiated Human Hepatoma Cells and of Appropriate Epstein–Barr Virus–Based Shuttle Vectors", 1989, *Gene,* 76:27–39.

(List continued on next page.)

*Primary Examiner*—Mindy Fleisher
*Assistant Examiner*—Terry A. McKelvey
*Attorney, Agent, or Firm*—Banner & Witcoff, Ltd.

[57] ABSTRACT

Episomal plasmids containing a papovavirus origin of replication and a papovavirus large T antigen mutant form are shown to replicate episomally in human cells, and yield levels of gene expression proportional to their episomal copy number. Candidate oncogenes and anti-oncogenes can be identified by transfecting the episomal plasmids containing a candidate oncogene or anti-oncogene into non-tumorigenic cells and screening for a tumorigenic phenotype.

2 Claims, 7 Drawing Sheets

OTHER PUBLICATIONS

Rio, et al., "A Mammalian Host–Vector System That Regulates Expression and Amplification of Transfected Genes by Temperature Induction", 1985, *Science,* 227:23–28.

Chittenden, et al., "Regulated Replication of an Episomal Simian Virus 40 Origin Plasmid in COS7 Cells", 1991, *J. Virol.,* 65:5944–5951.

Lusky, et al., "Inhibition of SV40 Replication in Simian Cells by Specific pBR322 DNA sequences", 1981, *Nature,* 293:79–81.

Roberts, et al., "Cis–Acting Negative Control of DNA Replication in Eukaryotic Cells", 1988, *Cell,* 52:397–404.

Mann, et al., "Cross–Reaction of BK Virus Large T Antigen with Monoclonal Antibodies Directed Against SV40 Large T Antigen", 1984, *Virology,* 138:379–385.

Arthur, et al., "Association of BK Viruria with Hemorrhagic Cystitis in Recipients of Bone Marrow Transplants", 1986, *N. Engl. J. Med.,* 315:230–234.

Dyson, et al., "Large T Antigens of Many Polyomaoviruses are Able to Form Complexes with the Retinoblastoma Protein", 1990, *J. Virol.,* 64:1353–1356.

DeCaprio, et al., "SV40 Large Tumor Antigen Forms a Specific Complex with the Product of the Retinoblastoma Susceptibility Gene", 1988, *Cell,* 54:275–283.

Chen, et al., "Identification of a Region of Simian Virus 40 Large T Antigen Required for Cell Transformation", 1990, *J. Virol.,* 64:3350–3357.

Chen, et al., "T–Antigen Mutant Activities In Vivo: Roles of p53 and pRB Binding in Tumorigenesis of the Choroid Plexus", 1992, *Oncogene,* 7:1167–1174.

Dalrymple, et al., "BK Virus T Antigens Induce Kidney Carcinomas and Thymoproliferative Disorders in Transgenic Mice", 1990, *J. Virol.,* 64:1182–1191.

Nakshatri, et al., "Functional Role of BK Virus Tumor Antigens in Transformation", 1988, *J. Virol.,* 62:4613–4621.

Caputo, et al., "Transactivation of BKV and SV40 Early Promoters by BKV and SV40 T–Antigens", 1986, *Virology,* 152:459–465.

Whitesell, et al., "Episome–Generated N–myc Antisense RNA Restricts the Differentiation Potential of Primitive Neuroectodermal Cell Lines", 1991, *Mol. & Cell. Biol.,* 11:1360–1371.

Baker, et al., "Suppression of Human Colorectal Carcinoma Cell Growth by Wild–Type p53", 1990, *Science,* 249:912–915.

Grossi, et al., "New BK Virus Episomal Vector for Complementary DNA Expression in Human Cells", 1988, *Arch. Virol.,* 102:275–283.

Pipas, et al., "Mutational Analysis of Simian Virus 40 T Antigen: Isolation and Characterization of Mutants with Deletions in the T–Antigen Gene", 1983, *Mol. & Cell. Biol.,* 3:203–213.

Braithwaite, et al., "Mouse p53 Inhibits SV40 Origin–Dependent DNA Replication", 1987, *Nature,* 329:458–460.

Wilcock, et al., "Localization of p53, Retinoblastoma and Host Replication Proteins at Sites of Viral Replication in Herpes–Infected Cells", 1991, *Nature,* 349:429–431.

Yang, et al., "BK Virus DNA: Complete Nucleotide Sequence of a Human Tumor Virus", 1979, *Science,* 206:456–462.

Cooper, et al., "Efficient Expression Vector for Human Transitional Carcinoma Cells," *Human Gene Therapy,* 4:557–566, 1993.

Sambrook, et al., *Molecular Cloning,* A Laboratory Manual, 1989, pp. 16.3–16.73, Cold Spring Harbor Laboratory Press, Plainview, NY.

Kalderon, et al., *Virology,* 139:109–137 (1984).

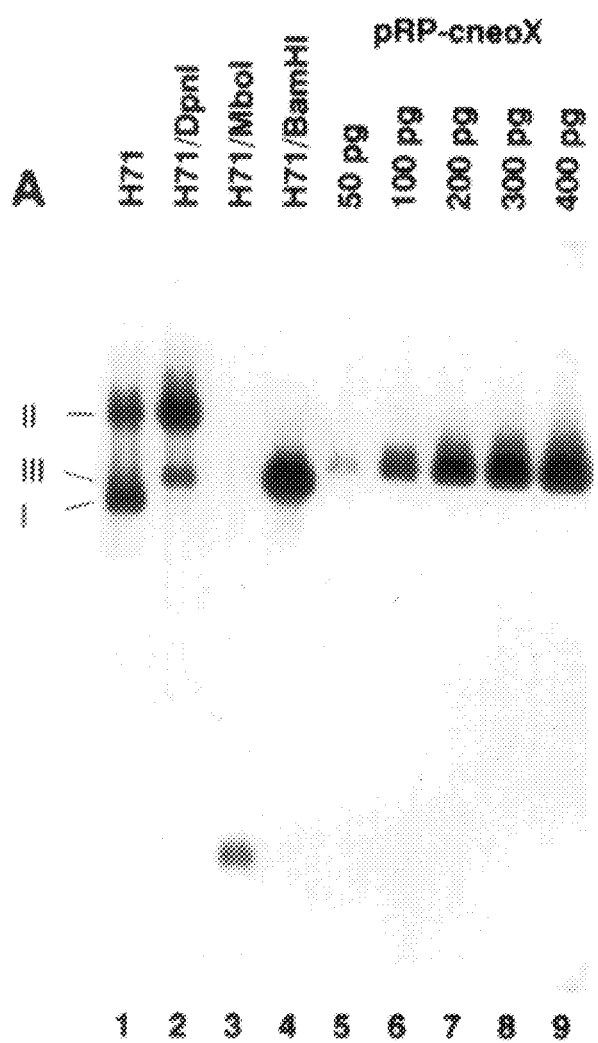
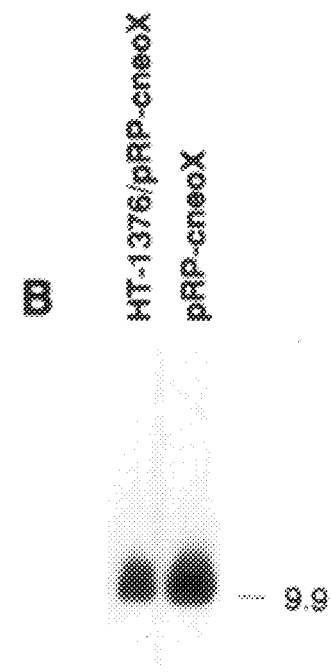
FIG. 1A
FIG. 1B 2.1 kb –

1 2 3 4

9.9 kb —

16.6 kb —

1 2 3 4 5 6

1 2 3 4 5 6 7

4,770,374

METHODS FOR IDENTIFYING ONCOGENES AND ANTI-ONCOGENES

This application is a continuation of application Ser. No. 08/479,204 filed Jun. 7, 1995 and a continuation of application Ser. No. 08/594,299 filed Jan. 30, 1996, which is a continuation of application Ser. No. 08/151,387, filed Nov. 12, 1993, now abandoned, said application Ser. No. 08/479,204 filed Jun. 7, 1995 which is a continuation of application Ser. No. 08/151,387, filed Nov. 12, 1993, now abandoned.

The work leading to this invention was supported in part by Grant No. P30 CA43703 from the National Institutes of Health. The U.S. Government may retain certain rights in this invention.

BACKGROUND OF THE INVENTION

1. Field of the Invention

This invention is directed to papovavirus-derived episomes that replicate efficiently in mammalian cells, yielding stable transfectants having a high episomal copy number and expressing encoded genes at high levels. Papovavirus-derived episomes may be useful in gene therapy strategies to modulate the growth of bladder carcinoma cells.

2. Review of Related Art

One approach to gene therapy of human cancer cells is to introduce vectors expressing antisense sequences to block expression of dominant oncogenes and growth factor receptors. However, high-level expression of the oncogenes requires comparable levels of antisense expression, which presents a considerable technical obstacle, particularly when using expression vectors having a limited potential for achieving multiple copies in stable transfectants. Human cells transduced by retroviral vectors have only one or several copies of integrated retrovirus in stable transfectants. In contrast, hundreds of copies of episomal plasmids can accumulate in stable transfectants because these vectors replicate extrachromosomally. One method to express high levels of antisense transcripts is to utilize episomal plasmid vectors than can replicate extrachromosomally in human cells.

Attempts to produce episomal vectors that will replicate in some types of human cells are reported by the literature. Episomal plasmids have been developed from several DNA viruses, including bovine papilloma virus (BPV) (Sarver, et al., 1981, *Mol. Cell. Biol.*, 1:486–496; DiMaio, et al., 1982, *Proc. Natl. Acad. Sci., U.S.A.*, 97:4030–4034), SV40 (Tsui, et al., 1982, *Cell*, 30:499–508), Epstein-Barr virus (EBV) (Yates, et al., 1985, *Nature*, 313:812–815; Margolskee, et al., 1988, *Mol. Cell. Biol.*, 8:2837–2847; Belt, et al., 1989, *Gene*, 84:407–417; Chittenden, et al., 1989, *J. Virol.*, 63:3016–3025), and BK virus (BKV) (Milanesi, et al., 1984, *Mol Cell. Biol.*, 4:1551–1560). Each of these episomal plasmids contains a viral origin of DNA replication and a virally encoded early gene that trans-activates the viral origin and allows the episome to replicate in the transfected host cell.

Although EBV-based episomes have been used to efficiently screen cDNA libraries, the EBV system has limited applications to non-lymphoid cell types (Vidal, et al., 1990, *Biochim. Biophys. Acta* 1048:171–177)), and the EBV replicon is not active in many cell types. Additionally, EBNA-1 is one of several EBV latent genes that immortalize human lymphocytes, and transfection of the EBV-negative BJAB lymphoma cell line by EBNA-1 induces soft agar growth, indicating transformation of the cells. (Konoshita, 1990, *Hokkaido Igaku Zasshi*, 65:362–375)

Furthermore, stable transfection efficiencies for EBNA-1 negative cell lines transduced by EBV episomal plasmids encoding EBNA-1 (transactivator) and ORI-P (EBV DNA origin) are low, not significantly better than non-episomal plasmids (Yates, et al., 1985; Vidal, et al., 1990. However, if EBNA-1 is expressed in cells prior to transfection, then a subsequent transfection with a plasmid containing ORI-P and a selectable marker can yield stable transfection efficiencies of up to 10% (Margolskee, et al., 1988; Belt, et al., 1989; Yates, et al., 1984, *Proc. Natl. Acad. Sci. USA* 81:3806–3810; Lutfallia, et al., 1989, *Gene* 76:27–39). Comparable results have been noted in a related system of COS cell clones expressing high levels of SV-T, which permit efficient replication of SV40 origin-containing plasmids in transient transfectants (Tsui, et al., 1982; Rio, et al., 1985, *Science*, 227:23–28; Chittenden, et al., 1991, *J. Virol.* 65:5944–5951).

In the COS cell system, however, episomal replication can proceed in a runaway fashion, resulting in up to $10^4$ episomal copies by 48 hours after transfection. Despite efficient episomal replication in transient transfectants, low stable transfection efficiencies have been noted in these studies (Chittenden, et al., 1991; Roberts, et al., 1986, *Cell*, 46:741–752). Presumably, most transient transfectants die secondary to episome-mediated cell death (Chittenden, et al., 1991; Roberts, et al., 1986).

However, transfection of COS cells by SV40 DNA origin-containing plasmids does produce stable transfectants having episomal plasmids (Tsui, et al., 1982), and it may be possible to control runaway episomal replication by a variety of strategies, including use of replication control regions from other viruses. For example, runaway episomal replication in COS cell clones can be controlled by use of plasmids containing the SV40 DNA origin and regions of the bovine papilloma virus (BPV) replicon (Roberts, et al., 1986; Roberts, et al., 1988, *Cell* 52:397–404). These studies have identified two BPV sequences (NCOR I and NCOR II) that modulate runaway SV40 episomal replication in transient transfectants, and a third trans-suppressing factor encoded by 5' sequences in the E1 open reading frame. Hybrid plasmids encoding the SV40 DNA origin and a 2113 bp EcoR1 fragment of BPV have substantially higher stable transfection efficiencies than pSV-NEO (Roberts, et al., 1986). A DNA homology search failed to identify similar NCOR sequences in the BKV or SV40 replicon.

Thus, there remains a need for vectors which will replicate episomally in a controlled fashion in mammalian cells for gene therapy applications. In particular, there is a need for vectors that will replicate episomally in human cells without transforming the cells.

SUMMARY OF THE INVENTION

It is an object of this invention to provide a vector which will reproduce episomally in a mammalian cell without transforming the cell.

It is another object of this invention to provide a method for gene therapy whereby a foreign gene, encoded on a vector that replicates episomally in high copy number without transforming transfected cells, is expressed in a mammalian cell transfected by the episomal vector.

It is still another object of this invention to provide a mutant form of papovavirus large T antigen that is replication-competent and transformation-negative.

In order to achieve these and other objects, the present invention provides a mammalian vector which is replication-competent and transformation-negative, the vector comprising at least one papovavirus origin of replication, preferably the origin from SV40 or BK virus, and a DNA sequence encoding a mutant form of papovavirus large T antigen which contains a replication-competent binding site for the origin of replication but which is negative for binding to at least one of wild-type p53 or retinoblastoma tumor suppressor (RB) gene products, preferably both, the DNA sequence being operatively linked to a homologous or heterologous promoter. In alternative embodiments of the vector, the DNA sequence encoding a mutant form of papovavirus large T antigen is operationally linked either to a papovavirus early promoter, to a promoter which is inducible, or to a promoter which is under hormonal control.

In another embodiment, this invention provides a method of expressing a foreign gene in a mammalian cell comprising transfecting the mammalian cell with a replication-competent, transformation-negative vector comprising at least one papovavirus origin of replication, a first DNA sequence encoding a mutant form of papovavirus large T antigen which contains a replication-competent binding site for the origin of replication but which is negative for binding to at least one of wild-type p53 or retinoblastoma tumor suppressor gene products, the DNA sequence being operatively linked to a first promoter, and a second DNA sequence encoding the foreign gene operatively linked to a second promoter; and expressing the foreign gene in the transfected cell. In preferred embodiments of this method, the papovavirus origin of replication is either the BK virus origin of replication or the SV40 origin of replication, and the mutant form of papovavirus large T antigen is a mutant SV40 large T antigen that binds to both SV40 and BK virus origins of replication but is negative for binding wild-type p53 and also negative for binding to retinoblastoma tumor suppressor gene product. In alternative embodiments, the mammalian cell is transfected by the vector in vitro, then the cell is introduced into a mammal and the foreign gene is expressed in vivo, or the vector is administered to a mammal and cells of the mammal are transfected in vivo, the foreign gene being expressed by these cells.

In another embodiment, the invention provides a DNA sequence encoding a mutant form of SV40 large T antigen which contains a replication-competent binding site for SV40 origin of replication but is negative for binding to wild-type p53 and is also negative for binding to retinoblastoma tumor suppressor gene product. In a preferred embodiment, residue 107 of the mutant form of SV40 large T antigen encoded by the DNA sequence is lysine and residue 402 is glutamic acid.

A highly efficient episomal expression vector that replicates extrachromosomally in human cells has been developed. We have demonstrated that replication-competent, transformation-negative SV40 large T antigen mutants can successfully drive replication of plasmids containing the SV40 DNA origin or BK virus origin of DNA replication. A preferred vector is derived from BK virus (BKV), a small DNA virus having significant homology to SV40. The properties of BKV episomes characterized in stable bladder carcinoma cell line transfectants have shown that these vectors replicate extrachromosomally for at least 5 months; achieve a high stable copy number (150) without inducing episome-mediated cell death; have a very low rate of integration; transcribe genes in proportion to their copy number; are efficiently transferred to daughter cells during cell division; can be shuttled from Hirt supernatant DNA to bacteria; and even persist in bladder cell transfectants for several months without selection pressure. These properties demonstrate the feasibility of using this vector system to transfer genes to human cells.

This invention makes a significant advance in episomal vector technology by developing replication-competent, transformation-negative mutants of papovavirus large T antigen to drive replication of plasmids containing papovavirus origins of DNA replication, such as the SV40 or BKV DNA origins. Since replication-competent, transformation-negative mutants for other DNA origin transactivators (such as EBNA-1) are not currently available, this episomal expression system has the unique feature of permitting efficient episomal replication without induction of transforming properties in the host cell. This advance enables development of safe and efficient episomal vectors for human gene therapy applications. This episomal vector system may also have widespread in vitro applications, such as development of a cancer tumor progression assay, and has the potential to significantly advance development of efficient episomal vector systems for cDNA library cloning and in vitro expression of heterologous genes in human cells.

BRIEF DESCRIPTION OF THE DRAWINGS

FIGS. 1A and 1B show Southern analysis of HT-1376 cells stably transfected with the BKV episomal vector pRP-cneoX. Cells were evaluated following 71 days of G418 selection. FIG. 1A. Hirt DNA from $3 \times 10^5$ cells was loaded in lanes 1–4 and digested with restriction enzymes as indicated. Increasing amounts (50–400 pg) of BamHI-digested pRP-cneoX plasmid were loaded in lanes 5–9. FIG. 1B. Total cellular DNA (10 pg) from these same HT-1376/pRP-cneoX stable transfectants was digested with BamHI (lane 1). In lane 2 is 500 pg of BamHI-digested pRP-cneoX plasmid. Hybridization probe in both panels was $^{32}$P-labelled pRP-cneoX.

DETAILED DESCRIPTION OF THE INVENTION

Figure 2A:
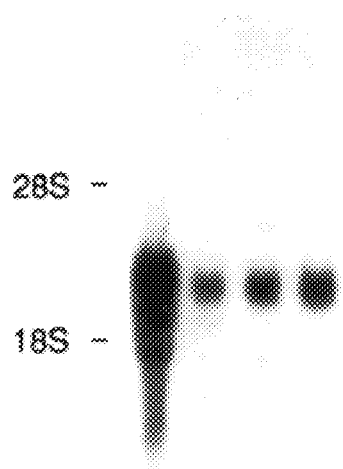
FIGS. 2A and 2B show expression of neomycin resistance gene mRNA in HT-1376 cells stably transfected with BKV episomal (pRP-cneoX, lane 1) and non-episomal (pSV2NEO, lanes 2–4) expression vectors. Hybridization probes: neomycin resistance gene (FIG. 2A), β-actin (FIG. 2B).

We have identified an episomal vector that efficiently replicates in transformed transitional epithelial cells (e.g., HT-1376 bladder carcinoma cell line). The vector (pRP-cneoX) contains a marker gene under control of the SV40 early promoter and a 3.2 kb segment of BKV which includes the BKV origin of replication and the BKV large T antigen under control of the BKV early promoter. Whereas the EBV episomal element was not active in HT-1376 transient transfectants, BKV episomes replicated extrachromosomally in these cells. More importantly, BKV episomes can replicate efficiently in HT-1376 cells without any apparent cellular toxicity, resulting in a high copy number of the episome in stable transfectants.

The copy number of BKV episome pRP-cneoX in HT-1376 cells stably transfected with this construct was approximately 150 copies per cell (see Example 1). This copy number compares to approximately 10–50 copies of EBV-derived episomes in lymphoblastoid cell lines and 10–80 copies of bovine papilloma virus- derived episomes in murine C127 cells (Sarver, et al., 1981; DiMaio, et al., 1982; Yates, et al., 1985). The high copy number of pRP-cneoX in HT-1376 transfectants is likely responsible for the efficient vertical transfer of pRP-cneoX to the progeny of these HT-1376 transfectants over multiple generations. The soft agar cloning efficiencies of HT-1376 cells transfected with either integrating vector pSV2NEO or pRP-cneoX, and plated in the presence or absence of G418, were essentially identical. These data indicate that episomal transfer of the neomycin resistance gene to daughter cells was as efficient as when this gene is integrated into HT-1376 genomic DNA. This result was not unexpected, since the probability that a given daughter cell would not contain at least one copy of the episome would be very low assuming random partitioning of the large number of plasmid copies during cellular division.

Our data demonstrate that a BKV episomal expression vector can produce very high levels of transcription of a transfected gene in HT-1376 cells. There was approximately a 20-fold increase in the steady-state level of neomycin resistance gene expression in pRP-cneoX transfectants compared to transfectants which had 5 integrated copies of pSV2NEO. Since the neomycin resistance gene is transcriptionally regulated by the SV40 early promoter in both constructs, these data demonstrate that BKV episomal vectors can produce significantly higher levels of expression of a transfected gene that plasmid vectors that must integrate into the host cell genome to produce stable transfectants. This difference is presumably due in part to the higher copy number of pRP-cneoX (150 copies) compared to pSV2NEO (5 copies) in HT-1376 transfectants.

Comparison of Episomal Vectors

BKV-derived episomes have several properties that are distinct from EBV, BPV, and SV40-derived episomes. Despite the significant amino acid homology between the large T antigens from BKV and SV40 (Mann, et al., 1984, Virol., 138:379–385), BKV episomes can yield stable, viable transfectants whereas SV40-based episomes replicate to such a high copy number that cell death typically ensues (Tsui, et al., 1982; Roberts, et al., 1986). This result may be due, in part, to differences in the level of T antigen present in these transfectants, characteristics of the DNA origins from these viruses, or presence of cis-regulatory sequences in the BKV episome that regulate DNA replication, as has been described in composite SV40-BPV-derived episomes (Roberts, et al., 1986; Hambor, et al., 1988, Proc. Natl. Acad. Sci. USA, 85:4010–4104).

Figure 3A:
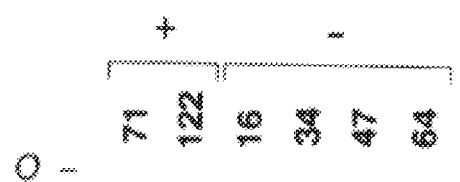
FIGS. 3A and 3B show that pRP-cneoX persists as an episomal plasmid in HT-1376 cells following withdrawal of selection pressure. Southern analysis of BamHI-digested Hirt supernatant DNA from $3 \times ^5$ HT-1376 pRP-cneoX transfectants grown in the presence (71 days, lane 1; 122 days, lane 2) or absence (16 days, lane 3; 34 days, lane 4; 47 days, lane 5; 64 days, lane 6) of G418. Hybridization probes were $^{32}$P-labeled pRP-cneoX (FIG. 3A) or a 343 bp $^{32}$P-labeled BamHI fragment of mouse mitochondrial DNA (ND1) obtained from pKSU1, a derivative of pAM1 (Martens, et al. 1979, *J. Mol. Biol.*, 327–351) (panel B).

Significantly, BKV episomes appear to replicate once per cell cycle in stable transfectants, because the pRP-cneoX copy number reaches a stable plateau of approximately 150 copies per cell. Stable copy number is also characteristic of EBV and BPV-derived episomes, which can similarly yield viable, stable transfectants, albeit at lower copy number. In contrast to EBV-derived episomes (Yates, et al., 1984; Hambor, et al., 1988), however, the copy number of BKV episomes is maintained at unreduced levels after 2 months of growth in the absence of selection pressure. Fluctuations in pRP-cneoX copy number during the time course of G418 withdrawal (shown in FIG. 3) presumably represent a dynamic interplay between factors predisposed to maintain the presence of episomes (such as efficient episomal replication during the cell cycle and potential growth advantages present in cells expressing BKV large T antigen) and factors that may reduce episomal copy number (such as unequal partitioning of the episome during cell division, or destruction by cellular nucleases). Comparable to BKV episomes, BPV episomes can also be maintained at stable copy numbers in unselected, transformed C127 transfectants (Sarver, et al., 1981; DiMaio, et al., 1982). However, the higher copy number of BKV episomes in unselected transfectants is an advantage in strategies to utilize these episomes for gene therapy.

I. Definitions

In describing the present invention, the following terminology is used in accordance with the definitions set out below.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., an intron-free coding sequence (cDNA) where the genomic coding sequence contains introns, or synthetic sequences having codons different than the native gene). Allelic variations or naturally occurring mutational events do not give rise to a heterologous region of DNA as defined herein.

A DNA "coding sequence" is a DNA sequence which is transcribed and translated into a polypeptide in vivo when placed under the control of appropriate regulatory sequences. A polyadenylation signal and transcription termination sequence will usually be located 3' to the coding sequence. A "promoter" is a DNA regulatory region capable of binding RNA polymerase in a cell and initiating transcription of a downstream (3' direction) coding sequence. A coding sequence under the control of a promoter in a cell is transcribed by RNA polymerase after the polymerase binds the promoter, the coding sequence being transcribed into mRNA which is then in turn translated into the protein encoded by the coding sequence.

"Transfection" of a cell occurs when exogenous DNA has been introduced inside the cell membrane. "Transformation" occurs when a cell population from primary cells or a cell line that only undergoes a finite number of divisions becomes immortalized, or when an immortal cell line acquires additional tumorigenic properties. Transformation can be detected by, for example, the ability of the transformed cell to form clones in soft agar or to form tumors in nude or SCID mice. A "clone" is a population of cells derived from a single cell or common ancestor by mitosis.

A "replicon" is any genetic element (e.g., plasmid, chromosome, virus) that functions as an autonomous unit of DNA replication in vivo.

A "vector" is a replicon, such as plasmid, phage or cosmid, to which another DNA segment (a heterologous segment) may be attached so as to bring about the replication of the attached segment.

An "episome" is a low molecular weight DNA molecule that resides in a cell separated from the cell's chromosome(s). Episomes replicate independently of mitotic replication of the chromosomes, being transmitted to daughter cells as part of the random reassortment of cellular contents during cell division. "Copy number" is the number of duplicate DNA molecules existing in an individual cell as episomes or is the number of duplicate sequences in the genome. Bacterial episomes are usually called plasmids.

"Foreign genes" are genes that are not found in the genome of the individual host cell. Foreign genes may be from the same species as the host or from different species. Where this invention describes transfection of a cell using DNA containing a foreign gene with the intent that the foreign gene will be expressed in the cell, the DNA will, of course, contain any control sequences necessary for expression of the foreign gene in the required orientation for expression.

Two DNA sequences that are substantially homologous can be identified by their ability to hybridize with each other in a Southern hybridization experiment, for example, under stringent conditions as defined for that particular system. Defining appropriate hybridization conditions is within the skill of the art. See e.g., Maniatis et al., supra; DNA Cloning, vols. 1 and II supra; Nucleic Acid Hybridization, supra.

II. Description of the Vector

A. Papovaviruses

Papovaviruses are DNA viruses with double-stranded, covalently closed, circular genomes of approximately 5000 bp and icosahedral capsids containing three viral proteins. The papovaviruses infect a variety of hosts, including humans (BK virus and JC virus ), monkeys (simian vacuolating virus (SV40) and lymphotropic papovavirus), baboon (simian agent 12), mouse (polyoma virus and K virus), hamster (hamster papovavirus), rabbit (rabbit kidney vacuolating virus), and budgerigar (budgerigar fledgling disease virus). These viruses have been judged to be related based on nucleotide sequence comparisons.

The viral genome is divided into early and late transcription regions, and contains a single origin of replication. Transcription begins from promoters near the origin of replication and proceeds bidirectionally—one direction for early transcripts and the other direction for late transcripts. The late transcriptional region encodes coat proteins (VP1, VP2, and VP3). The early transcriptional region encodes the T antigens, particularly the large T antigen which functions in viral DNA replication. The large T antigen also down-regulates early transcription by binding to viral DNA near the early promoter, activates cellular genes involved in DNA synthesis, and transforms primary cells in tissue culture.

Viral DNA replicates in the nucleus as "minichromosomes," but viral DNA can replicate many times in a single cellular S phase. Viral DNA replication is initiated by the large T antigen, independently of its stimulation of cellular DNA synthesis. The large T antigen binds to viral DNA in the neighborhood of the origin of replication and unwinds the DNA helix, which is required for viral DNA replication. New viral DNA is then synthesized by cellular enzymes.

B. Episomal Amplification Cassette

To provide enhanced expression in gene therapy applications, episomal vectors must replicate extrachromosomally without transforming the transfected cell. This invention provides a replication cassette for such containing the essential elements of papovavirus replication. The replication cassette (or episomal amplification cassette) contains 1) a papovavirus origin of DNA replication (ORI); 2) a replication-competent, transformation-negative mutant form of the papovavirus large T antigen; and 3) a promoter to drive expression of the mutant T antigen. When the replication cassette of this invention is coupled with other DNA sequences in a circular DNA molecule, the DNA molecule will be replicated episomally by mammalian cells after transfection.

The initial BKV episomal vectors reported by Milanesi, et al. (1984), contained a 3.2 kb fragment of BKV including the origin of DNA replication and the BKV large T antigen transcriptionally regulated by the BKV early promoter.

As taught below and exemplified in the Examples, the BKV. expression system may be modified according to this invention, so that it does not induce soft agar growth in nontumorigenic cells, yet retains the ability to replicate extrachromosomally. The components of the replication cassette will be selected according to the following criteria and assembled as described below.

1. Origin of Replication

The origin of replication in the replication cassette is selected from ORI sequences of one of the papovaviruses. DNA replication initiated at these loci is sensitive to control by the large T antigen of the same virus, and to a similar or lesser extent by large T antigen of other papovaviruses.

In the presence of a compatible large T antigen, the papovavirus origin will drive episomal replication. The origin/large T antigen combination should be tested to determine whether they drive replication of the episome. One simple test for replication competency is to transfect a population of cells which express the large T antigen mutant proposed for the replication cassette with a vector containing the proposed origin of replication and then monitor the transfected cells for synthesis of episomal DNA by Southern blot (see, e.g., Example 6C).

Particularly preferred is the BKV origin, which has been demonstrated to drive episomal replication with either BKV large T antigen (BK-T) or SV-T. Other preferred origins are those that drive replication in primates, including SV40, JC virus, lymphotropic papovavirus, and simian agent 12. Any papovavirus origin of replication that can be shown to drive episomal replication in human cells will be suitable for the replication cassettes of this invention.

The BKV replicon is active in the HT-1376 bladder carcinoma cell line, whereas. the Epstein-Barr virus (EBV) replicon is not functional in these cells. BKV has a trophism for human uroepithelial cells (Arthur, et al., 1986, *N. Engl. J. Med.*, 315:230–234), and an episomal vector derived from BKV will replicate efficiently in human bladder carcinoma cell lines. Hybrid SV40/BK virus-derived episomes replicated extrachromosomally in the nontumorigenic 5637 bladder cell line. These data suggest that the tissue tropism of viruses from which episomal constructs are derived may predict the cell type in which episomal constructs are active.

2. Large T Antigen Mutants

The replication activity of BKV episomes is dependent on expression of the BK-T. BK-T has a 75% amino acid homology to the SV40 large T antigen (SV-T) (Yang, et al., 1979), a protein having well-described immortalization and tumorigenic properties (Shin, et al., 1975, *Proc. Natl. Acad. Sci. USA*, 72:4435–4439; Christian, et al., 1987, *Cancer Res.*, 47:6066–6073; Michalovitz, et al., 1987, *J. Virol.*, 61:2648–2654; Hanahan, et al., 1989, *Science*, 246:1265–1275; DeCaprio, et al., 1988, *Cell*, 54:275–283; Chen, et al., 1990, *J. Virol.*, 64:3350–3357; Chen, et al., 1992, *Oncogene*, 7:1167–1175). Similar to SV-T, BK-T can bind to and thereby inactivate wild-type p53 and retinoblastoma (RB) tumor suppressor gene products (Mann, et al., 1984; Dyson, et al., 1990, *J. Virol.* 64:1353–1356), the primary proposed mechanism by which these T antigens induce tumorigenic properties (DeCaprio, et al., 1988; Chen, et al., 1992). Transgenic mice expressing BK-T develop renal carcinomas and thymoproliferative disorders (Dalrymple, et al., 1990, *J. Virol.*, 64:1182–1191), and BK-T can transform NIH 3T3 cells and baby rat kidney cells (Nakshatri, et al., 1988, *J. Virol.*, 62:4613–4621). It is therefore possible that BKV episomal vectors containing wild-type BK-T could confer tumorigenic properties to some nontumorigenic cell lines, making such an episomal vector unsuitable for use in gene therapy, because the vector may be able to confer soft agar growth on cells in culture or induce neoplastic transformation in vivo.

However, the significant homology between SV-T and BK-T led to a specific strategy to solve this problem. SV-T can bind to the BKV origin of replication in vitro and can stimulate the replication of a plasmid containing the BKV origin of replication in COS cells (Ryder, et al., 1983, *Virol.*, 129:239–245; Deyerie, et al., 1989, *J. Virol.*, 63:356–365). Therefore, replication-competent SV-T mutants having suppressed transformation properties were examined as substitutes for BK-T to promote replication of BKV episomes without transformation.

Replication-competent, transformation-negative SV-T mutants.

The domain of SV-T which binds the SV40 DNA origin is separate and distinct from the RB and p53 binding domains, as illustrated in Example 6 below. Three replication competent, transformation negative SV-T mutants are also illustrated. The first SV-T mutant is 107-T (also referred to as K1, Kalderon, et al., 1984, *Virol.*, 139:109–137), which is replication competent yet nontumorigenic in several cell types (DeCaprio, et al., 1988; Chen, et al., 1990; Chen, et al., 1992; Kalderon, et al., 1984; Cherington, et al., 1988, *Mol Cell Biol.*, 8:1380–1384). 107-T differs from wild-type SV-T in a single base pair resulting in substitution of lysine for glutamic acid in codon 107. Codon 107 is in the RB binding domain of SV-T, and the inability of 107-T to bind RB most likely accounts for its nontumorigenic properties. The DNA binding region of 107-T is intact, however, and as shown below, we have determined that 107-T can drive replication of a test plasmid containing the SV40 DNA origin.

The second mutant is 402-T, which has a substitution of glutamic acid for asparagine in codon 402 (Lin, et al., 1991, *J. Virol.*, 65:2066–2072). The 402-T point mutation is in the p53 binding domain of SV-T, and 402-T fails to bind wild-type p53, although it appears to bind RB, and can also drive replication of the SV40 DNA origin. 402-T is non-transforming in human diploid fibroblast lines D.551 and WI-38 (Lin, et al., 1991, *J. Virol.*, 65:6447–6453).

Lastly, a novel SV-T mutant has been constructed which contains both point mutations found in 107-T and 402-T (107/402-T). This SV-T mutant will not bind either p53 or RB, and will have very low potential to confer tumorigenic properties. Replication competent 107/402-T will have particular value.

Integrating vectors encoding these three different SV-T mutants which have differing abilities to bind to wild-type p53 and RB have been prepared, and these SV-T mutant vectors have been transfected into nontumorigenic bladder cell lines. Single cell clones have been characterized which express the mutant SV-T molecules, yet remain nontumorigenic, and some of these clones have been shown to drive replication of plasmids containing SV40 DNA origins. This strategy has therefore been successful in modifying a papovavirus large T antigen for use in episomal vectors carrying an SV40 replicon for efficient expression of foreign genes in nontumorigenic cells.

The large T antigen mutants encoded by replication cassettes of this invention must be replication-competent and transformation-negative, that is they must induce DNA replication and not transform the host cell. Trans-activation of DNA replication can be tested using Southern blot analysis of Hirt supernatant or total cellular DNA extracted from transient episomal transfectants, as described above.

The transforming activity of the mutant large T antigen can be tested directly (see, e.g., Nakshatri, et al. 1988) or cells transfected with an expression vector expressing the mutant T antigen can be tested for soft agar cloning activity or growth in nude or SCID mice to determine whether the mutant T antigen is transformation-negative. Alternatively, mutants may be selected based on negative binding studies with wild-type p53 and wild-type RB. One suitable assay measures binding by generating in vitro translated mutant large T antigen protein and mixing it with authentic wild-type p53 or RB (e.g. in vitro translated or baculovirus produced) before immunoprecipitation with antisera to p53 or RB, respectively, to immunoprecipitate these proteins and any T antigen proteins complexed to them. Western blots of the immunoprecipitate may be developed with antisera to large T antigen, which will detect mutant T antigens that are positive for binding.

An alternative procedure would be transfecting a population of mammalian cells expressing wild-type p53 and RB (preferably from a human cell line) with an expression vector so that the cells express the large T mutant (as detected by, e.g., binding to antisera for T antigen). The cells are then lysed and the lysate treated with antisera to p53 or RB. The immunoprecipitate is treated as before. This latter assay has some potential for false-negatives if, for instance, the amount of mutant T antigen expressed is significantly different from the amount of p53 or RB present, or if there are subtle mutations in the p53 or RB expressed by the test cell, but it more closely approximates the in vivo conditions.

A particularly preferred mutant large T antigen is the SV-T mutant 107/402-T described above. Other mutants of SV-T and other papovavirus large T antigens have been described in the literature, and additional mutants can be generated by well-known recombinant DNA techniques. These mutants will be suitable for the replication cassette of this invention, so long as they are replication-competent and transformation-negative as determined by the above tests.

3. Promoters

In general, replication-competent, transformation-negative papovavirus large T antigen will be transcriptionally regulated by either heterologous or homologous promoters. The heterologous promoters are usually promoters which are active in mammalian cells, such as mammalian promoters and mammalian viral promoters. Where the episomal amplification cassette is part of an episomal expression vector for gene therapy application, the promoter will, of course, be chosen to be active in the cell which is the target for expression of the foreign gene.

Some heterologous promoters, such as CMV immediate early promoterenhancer, are not down-regulated by T antigen, thereby maximizing T antigen expression and consequently, episomal replication. This may be particularly advantageous in transient transfection strategies for gene therapy applications in which high level gene expression is desirable. Alternatively, use of homologous papovaviruses promoters, which are down regulated by T antigen, may constrain runaway episomal replication, thereby achieving controlled, stable expression. Such a promoter/T antigen/ origin combination will provide high copy number, stable episomes in transfected cells.

Alternatively, the promoter controlling expression of the mutant large T antigen may be selected to regulate episomal replication. For example an inducible promoter (such as the metallothionen promoter) may be used, and replication of the episome will be amplified in the presence of the inducer. Alternatively, a promoter for a developmentally-controlled or tissue-specific gene (e.g., the breast specific promoter for the whey acidic protein gene, Shoeneberger, et al., 1988, *EMBO J.*, 7: 169–175) may be used to limit the amplification of the episome copy number to certain cell types where that promoter is active. In gene therapy using an episome which carries a foreign gene whose expression level is proportional to copy number, selection of the promoter controlling T antigen expression provides a measure of therapeutic control of expression.

4. Vectors for Insertion of Cassettes

Broadly, the vectors into which the replication cassette of this invention may be inserted may be any vector that will carry the cassette, and any associated foreign genes, into mammalian cells in which the particular papovavirus origin and large T antigen will drive replication of the vector. The vector, of course, will not contain any sequences that prevent replication from the papovavirus origin of replication in mammalian cells or prevent expression of any foreign gene inserted into the vector for gene therapy applications. Suitable vectors include bacterial plasmids, which are useful as shuttle vectors to produce large quantities of the vector containing the replication cassette in bacterial culture for subsequent use in transfection of mammalian cells. Other suitable vectors include well-known mammalian vectors, usually of viral origin, which are known to transfect mammalian cells, and are non-pathogenic, or of limited pathogenicity, including defective or mutant viruses (see, e.g., Hock, et al. 1986, *Nature*, 320:275–277;

Sorrentino, et al. 1992, *Science*, 257:99–103; Bayle, et al. 1993, *Human Gene Therapy*, 4:161–170; Le Gal La Salle, et al. 1993, *Science*, 259:988–990; Quantin, et al. 1992, *Proc. Natl. Acad. Sci. USA*, 89:2581–2584; Rosenfeld, et al. 1992, *Cell*, 68:143–155). Where the vector is a mammalian virus, it is of course important that insertion of foreign genes into the viral genome does not destroy viral infectivity. Selection of a particular vector will take into account the particular mammal and the particular cell type in which episomal amplification is desired, and the skilled worker can readily select suitable vectors from among many available in art. (See, e.g., Sambrook, et al., 1989, "Molecular Cloning: A Laboratory Manual"; Miller, et al., 1989, *BioTechniques*, 7:980–990; Salmons, et al., 1993, *Human Gene Therapy*, 4:129–141; Stratford-Perricaudet, et al., 1991, in "Human Gene Transfer," Cohen-Haguenauer, et al., eds., John Libbery Eurotest Ltd. 219:51–61).

III. Method of Constructing the Vector

A. Sources of Component DNA Sequences

The DNA sequences of various papovaviruses are described in the literature, including the DNA sequences encoding the origin of replication, the early promoter, and the large T antigen. (See, e.g., (for SV40) Subramanian, et al. 1977, *J. Biol. Chem.*, 252:355–367; Reddy, et al. 1978, *Science*, 200:494–502; Fiers, et al. 1978, *Nature*, 273:113–120; Van Heuverswyn, et al. 1978, *Eur. J. Biochem.*, 100:51–60; (for BKV) Yang, et al. 1979, *Science*, 206:456–461; Deyerle, et al. 1989, *J. Virol.*, 63:356–365; (for hamster papovavirus) Delmas, et al. 1985, *EMBO J.*, 4:1279–1286; (for JC virus) Frisque, et al. 1984, *J. Virol*, 51:458–469; (for polyoma) Zhu, et al. 1984, *J. Virol.*, 51:170–180.) Clones containing many of the sequences are contained in various mammalian vectors available from commercial suppliers, such as Stratagene, Gibco-BRL Life Technologies, United States Biochemicals, and Promega. Clones containing the complete genomic sequence for BK virus, JC virus, K virus, polyoma virus, and SV40 are available from American Type Culture Collection, 12301 Parklawn Drive, Rockville, Maryland 20852, U.S.A. (ATCC). Clones containing promoters, bacterial origins of replication, and a variety of vectors are also available from the commercial sources listed above or ATCC, as well as other sources well known to those skilled in the art of recombinant DNA manipulation. Specific sequences encoding particular proteins or regulatory sequences may be obtained from these clones using standard recombinant DNA techniques, such as those described below. The particular foreign genes whose expression in mammalian cells is desired, and sources for sequences encoding them, will be readily apparent to those skilled in the art of gene therapy.

B. Recombinant Procedures For Vector Construction

The practice of the present invention employs, unless otherwise indicated, conventional molecular biology, microbiology, and recombinant DNA techniques within the skill of the art. Such techniques are well known to the skilled worker and are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover, ed., 1985);

"Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S.J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989).

DNA segments corresponding to the papovavirus origin of replication, the papovavirus large T antigen coding sequence and the papovavirus early promoter may be obtained from readily available recombinant DNA materials, such as those available from the ATCC, which include BK virus, JC virus, K virus, polyoma virus, and SV40 virus. DNA segments or oligonucleotides having specific sequences can be synthesized chemically or isolated by one of several approaches. The basic strategies for identifying, amplifying and isolating desired DNA sequences as well as assembling them into larger DNA molecules containing the desired sequence domains in the desired order, are well known to those of ordinary skill in the art. See, e.g., Sambrook, et al., (1989); B. Perbal, (1984). Preferably, DNA segments corresponding to the papovavirus origin, large T antigen and early promoter may be isolated individually using the polymerase chain reaction (M. A. Innis, et al., "PCR Protocols: A Guide To Methods and Applications," Academic Press, 1990). A complete sequence may be assembled from overlapping oligonucleotides prepared by standard methods and assembled into a complete coding sequence. See, e.g., Edge (1981) *Nature* 292:756; Nambair, et al. (1984) *Science* 223:1299; Jay, et al. (1984) *J. Biol. Chem.*, 259:6311.

The assembled sequence can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as those encoding foreign genes for gene therapy, bacterial origins of replication to make shuttle vectors (for-shuttling between prokaryotic intermediate hosts and mammalian final hosts), etc.

Procedures for construction and expression of mutant proteins of defined sequence are well known in the art. A DNA sequence encoding a known mutant of papovavirus large T antigen can be synthesized chemically or prepared from the wild-type sequence by one of several approaches, including primer extension, linker insertion and PCR (see, e.g., Sambrook, et al.). Alternatively, additional mutants can be prepared by these techniques having additions, deletions and substitutions in the wild-type sequence. In either case, it is preferable to test the mutants to confirm that they are replication-competent and transformation-negative, by the assays described above. Mutant large T antigen protein for testing may be prepared by placing the coding sequence for the polypeptide in a vector under the control of a promoter, so that the DNA sequence is transcribed into RNA and translated into protein in a host cell transformed by this (expression) vector. The mutant large T antigen protein may be produced by growing host cells transfected by an expression vector containing the coding sequence for the mutant T antigen under conditions whereby the polypeptide is expressed. The selection of the appropriate growth conditions is within the skill of the art.

C. Intermediate Stage Vectors

Preferably the vector containing the replication cassette will also contain a functional bacterial origin of replication and selection markers that function in bacteria (i.e., a shuttle vector). These will allow cloning of the vector in bacteria to provide a stable reservoir of the vector for storage and to facilitate amplification, where large quantities of the vector containing the replication cassette and any associated foreign genes can be recovered from bacterial culture. The procedures, as well as appropriate bacterial origins and selection markers are well known in the art (see, e.g. Sambrook, et al.). Alternatively, mammalian viral vectors may be amplified in mammalian cell culture, using well known techniques. Appropriate procedures for storage and standardization of preparations containing virus vectors or bacterial cells harboring shuttle plasmid vectors will be readily apparent to those skilled in the art.

D. Functional Tests of the Vector

Vectors containing the replication cassette of this invention will routinely be tested after they have been constructed to confirm that the vector is replication-competent and non-transforming. These tests will assure that sequences included in the vector do not interfere with the functioning of the replication cassette. Replication competence (i.e., that both the mutant large T antigen and the origin of replication are functional) is usually tested by transfecting a population of non-transformed cells of the target cell type with the vector and monitoring episomal DNA production by Southern blot. Stable transfectants from the replication test can be further tested for soft agar cloning activity or tumorigenesis in nude or SCID mice to confirm that the vector has not transformed the cells. Southern blots of DNA from the stable transfectants may be used to indicate whether they have integrated the vector into genomic DNA or if the vector is being carried as a stable episome.

IV. Use of the Vector

A. Therapeutic Use

Vectors for use in gene therapy are constructed by inserting the replication cassette of this invention into a suitable mammalian vector along with the foreign gene whose expression is desired, using standard recombinant DNA techniques as described above to produce an episomal expression vector. Cells are then transfected with these episomal expression vectors under conditions that maintain cell viability and the vectors replicate episomally in the cells. The episomal expression vectors may be administered to patients in a variety of ways.

In one embodiment cells are transfected with the episomal expression vector in vitro. Usually, appropriate cells are obtained from the patient, for instance peripheral blood monocytes from a blood sample, and these cells are transfected with the episomal expression vector before being re-introduced into the patient. Alternatively, stem cells in a population of the patient's cells are cultured to provide a large cell population, compatible with the patient, and the cells are transfected with the episomal expression vector in culture. Then the transfected cell population is re-introduced into the patient.

In another embodiment, the episomal expression vector is based on a mammalian virus which infects the patient mammal, containing a replication cassette according to this invention and a foreign gene. The viral episomal expression vector is administered to the patient, where it infects the patient's cells, and the episomal expression vector then replicates episomally in the cells.

In another embodiment, the episomal expression vector is introduced into the patient mammal in conjunction with liposomal or receptor-mediated delivery systems (see Felgner, et al., 1987, *Proc. Natl. Acad. Sci USA* 84:7413–7417 and Zhu, et al., 1993, *Science*, 261:209–211, incorporated herein by reference). Once the patients' cells are transfected in vivo, the episomal expression vector will replicate extrachromasomally.

Expression of the foreign gene may occur once the cell has been transfected by the episomal expression vector. Usually the foreign gene will be expressed constitutively, and the level of expression will be controlled by the copy number of the episome. In another embodiment, expression of the foreign gene will be under control of a promoter than can be up- or down-regulated in a manner described above for expression of the mutant large T antigen. Selection of suitable promoters for control of the foreign gene will be apparent to the skilled worker, based on the desired clinical result.

While any gene that can be expressed in a mammalian cell may be incorporated into a transfection vector as the foreign gene according to this invention, preferred genes will be those whose expression in a target cell population will counter-act a disease process. For example, an episomal gene therapy vector could be used to target the immune system to kill cancer cells in vivo. Tumor cell lines transfected with cytokine cDNA have been successfully used as cancer vaccines (Connor, et al., 1993, *J. Exp. Med.*, 177:1127–1134; Golumbek, et al., 1991, *Science*, 254:713; Porgador, et al., 1992, *Cancer Res.*, 52:3678; Aoki, et al., 1992, *Proc. Natl. Acad. Sci. USA*, 89:3850) and transfection of tumor cells in vivo with appropriate episomal vectors will enhance tumor kill, since episomal replication in the tumor cell will efficiently produce the desired high local concentration of cytokines, thereby stimulating immune effector cells. One such example is introduction of episomal expression vectors encoding interleukin-2 into bladder cancer cells in vivo via instillation of liposome/DNA complexes directly into the bladder lumen. Another example is transfection of lung cancer cells in vivo with interleukin-6 via inhalation of aerosolized liposome/DNA complexes (see Stribling, et al., 1992, *Proc. Natl. Acad. Sci. USA*, 89:11277–11281, for method using non-episomal vectors). Other gene therapy approaches to kill cancer cells include expression of genes conferring drug susceptibility, such as transfection with herpes simplex thymidine kinase encoding vectors followed by ganciclovir treatment. (Culver, et al., 1992, *Science*, 256: 1550–1552 used integrating vectors. Replacing the integrating vector with an episomal expression vector will enhance the level of susceptibility conferring enzyme.) Other foreign gene sequences whose expression by a patient's cells would counter-act a disease process will be apparent to those skilled in the art.

The presence of multiple copies of papovavirus-based episomes may increase expression of encoded genes compared to retroviral vectors, since only one to several copies of the retrovirus integrate per cell. Additionally, episomal DNA would be free of positional effects that may result in decreased expression from integrated vectors. The high level of transcription produced by episomal vectors of this invention may be particularly useful in antisense experiments, because high-level expression of antisense transcripts may be necessary to decrease translation of overexpressed target mRNA (Whitesell, et al., 1991, *Mol. Cell. Biol.*, 11:1360–1371).

The persistence of BKV episomes in pRP-cneoX/HT-1376 transfectants after withdrawal of selection pressure suggests that these vectors may be maintained for a reasonable period of time in human tissues. Even a transient period episomal replication may be sufficient for effective use of papovavirus episomes to treat patients with cancer. For example, wild-type anti-oncogenes capable of inducing apoptosis, such as p53 (Baker, et al., 1990, *Science*, 249:912–915; Shaw, et al., 1991, *Proc. Natl. Acad. Sci. USA*, 89:4495–4499), may need to be expressed for only a short period of time to kill transfected tumor cells. Similarly, transient expression of genes encoding susceptibility factors to chemotherapeutic agents may be effective in killing tumor cells, as has recently been demonstrated for herpes simplex thymidine kinase followed by gancyclovir treatment, and cytosine deaminase followed by 5'-fluorocytosine treatment (Culver, et al., 1992, *Science*, 256:1550–1552; Muller, et al., 1992, *Proc. Natl. Acad. Sci. USA*, 89:33–37). Furthermore, transient expression of cytokines, such as interleukin-4, may be effective in modulating the immune system to eliminate tumor cells (Golumbek, et al., 1991, *Science*, 254:713–716).

The episomal vector material is generally produced by culture of recombinant or transfected cells and formulated in a pharmacologically acceptable solution or suspension, which is usually a physiologically-compatible aqueous solution, or in coated tablets, tablets, capsules, suppositories, inhalation aerosols, or ampules, as described in the art, for example in U.S. Pat. No. 4,446,128, incorporated herein by reference. Administration may be any suitable route, including oral, rectal, intranasal or by intravesicular (e.g. bladder) instillation or injection where injection may be, for example, transdermal, subcutaneous, intramuscular or intravenous.

The vector-containing composition is administered to a mammal in an amount sufficient to transfect a substantial portion of the target cells of the mammal. Determination of the amount will involve consideration of infectivity of the vector, transfection efficiency in vitro, immune response of the patient, etc. A typical initial dose for administration would be 10–1000 micrograms when administered intravenously, intramuscularly, subcutaneously, intravesicularly, or in inhalation aerosol, 100 to 1000 micrograms by mouth, or $10^5$ to $10^{10}$ plaque forming units of a recombinant vector, although this amount may be adjusted by a clinician doing the administration as commonly occurs in the administration of other pharmacological agents. A single administration may usually be sufficient to produce a therapeutic effect, but multiple administrations may be necessary to assure continued response over a substantial period of time.

Further description of suitable methods of formulation and administration according to this invention may be found in U.S. Pat. Nos. 4,592,002 and 4,920,209, incorporated herein by reference.

B. Alternative Uses for Claimed Compositions

Episomal expression vectors according to this invention also have in vitro uses. For example, episomal expression vectors may be used to enhance production of proteins that are produced in mammalian cell culture, perhaps because they must be post-translationally glycosylated (e.g., Factor VIII). Transfecting the production cell population with an episomal expression vector containing a replication cassette prepared as described above and a foreign gene encoding the desired protein will increase the expression level of the desired protein, as episomal amplification leads to high copy number of the foreign gene in the production cells.

The episomal expression vectors of this invention may be used in studies to identify potentially novel dominant oncogenes and/or anti-oncogenes that are involved in tumor progression. By constitutively expressing cDNA clones at high levels, this approach may identify new genes or genes marking biological pathways that currently have not been shown to be involved in tumorigenesis. Moreover, this assay system will permit anti-sense cDNA library screening for tumor suppressor genes, greatly simplifying the currently labor intensive methods required to identify members of this class of genes.

This may be accomplished, for instance, by transfecting nontumorigenic bladder cell lines that do not clone in soft agar with cDNA derived from tumorigenic, anchorage independent cell lines, and phenotypically screening the transfectants for the ability to grow in soft agar. The cDNAs responsible for inducing nontumorigenic cells to clone in soft agar will then be identified by shuttling the episomal vector from bladder cell transfectants to bacteria. Second generation transfection studies will subsequently confirm the ability of candidate dominant oncogenes to fully transform nontumorigenic bladder cells. In a similar fashion, cDNA libraries from nontransformed cells screened in an anti-sense orientation could theoretically identify anti-oncogenes.

EXAMPLES

In order to facilitate a more complete understanding of the invention, a number of Examples are provided below. However, the scope of the invention is not limited to specific embodiments disclosed in these Examples, which are for purposes of illustration only.

Example 1

BKV episomal plasmids can stably replicate in HT-1376 cells

Plasmids pRP-cCATX and pRP-cncoX are BKV episomal plasmids that contain a 3.2-kb fragment of BKV encoding the origin of DNA replication and the large T antigen (Grossi, et al., 1988). pRP-cCATX encodes the chloramphenicol acetyltransferase (CAT) gene driven by the SV40 early promoter, whereas pRP-cncox encodes the neomycin resistance gene [phosphotransferase APH(3')II from transporon Th5] driven by the SV40 early promoter. pSV2CAT/220.2 is a derivative of pSV2CAT containing the EBV episomal element (Haver, et al., 1989). pSV2NEO encodes the neomycin resistance gene driven by the SV40 early promoter (Southern and Berg, 1982). pSV2CAT encodes the CAT gene transcriptionally regulated by the SV40 early promoter, and pSVOCAT is a derivative of pSV2CAT lacking the SV40 early promoter (Gorman, et al., 1982).

To evaluate if a BKV episomal plasmid can stably replicate in bladder carcinoma cells, HT-1376 cells were transfected with pRP-cneoX, a derivative of pSV2NEO containing a 3.2 kb episomal element consisting of the BKV origin of DNA replication and the BKV large T antigen (Grossi, et al., 1988, Arch. Virol., 102:275–283).

Transfection and Selection

A total of $1.5\times10^6$ cells in 60-mm dishes were transfected using 10 μg of plasmid DNA and 40 μg of lipofectin in 3 ml of Optimem (Gibco-Bethesda Research Labs, Gaithersburg, Md). Following 6 hours of incubation, DMEM was added with supplemental fetal calf serum to obtain a final concentration of 10%. Two days after transfection, cells were trypsinized and seeded in six-well plates, and 24 hours later 200 μg/ml G418 was added to the media to initiate selection.

Southern Blots

DNA from transfected cells was evaluated by Southern blot after 71 days of G418 selection, and the Southern blots were probed with $^{32}$P-labelled pRP-cneoX. Low-molecular-weight DNA (Hirt supernatant DNA) was prepared from HT-1376 transfectants as described by Hirt, 1967, J. Mol. Biol., 26:365–369). Total cellular DNA was removed from CsCl gradients and purified as previously described (Davis, et al., 1986, "Basic Methods In Molecular Biology", Elsevier Science Publishing, NY, pp. 130–135). Hirt supernatant and digested total cellular DNAs were electrophoresed in 0.7% agarose gels, transferred to Nytran membranes (Schleicher & Scheull, Keene, NH), hybridized to $^{32}$P-labeled random primed probes, and washed to a final stringency of 0.2X saline sodium citrate (SSC)/1.0% sodium dodecyl sulfate (SDS) at 65° C.

A. Episomal Replication in Stable Transfectants

Low molecular weight DNA (Hirt supernatant DNA) derived from these stable transfectants was subjected to Southern blot analysis, and the data, presented below in FIG. 1, Panel A, shows episomal plasmids. Plasmid forms II (nicked circular) and III (supercoiled) are evident in lane 1, indicating that free plasmid DNA is present in these transfectants. The pRP-cneoX episome in these Hirt supernatants is the same size as plasmid controls, indicating no detectable rearrangements or internal deletions of the episome as it is passaged in HT-1376 cells.

To confirm that this plasmid DNA is newly replicated episomal DNA, lanes 2 and 3 show Hirt supernatant DNA was digested with DpnI and MboI, respectively (Pipas, et al., 1983, Mol. Cell. Biol., 3:203–213). DpnI will cleave the GATC recognition site when both adenine bases are methylated, a feature of plasmid DNA synthesized in DNA adenine methylase (DAM) positive bacteria (input DNA). In contrast, MboI will cleave the GATC recognition sequence when adenine bases are not methylated. Since human cells lack the DAM enzyme, MboI digestion of Hirt supernatant DNA indicates that the episome replicated extrachromosomally. The lack of restriction fragments following DpnI digestion and the complete cleavage of Hirt supernatant DNA following MboI digestion confirms that the plasmid DNA present in these transfectants is newly replicated, episomal DNA.

B. There is a high copy number of BKV episomes in HT-1376 transfectants. To determine the copy number of episomes per cell, BamHI-digested Hirt supernatant DNA and a standard curve consisting of increasing amounts (50–400 pg) of BamHI-digested, linearized pRP-cneoX plasmid was evaluated by Southern blot analysis (FIG. 1, Panel A, lanes 4–9). Densitometric analysis of these bands indicates that there is approximately 500 pg of pRP-cneoX per $3\times10^5$ cells, or approximately 150 copies of the episome per cell. This copy number is higher than reported for most other episomal vectors. For example, a typical copy number of Epstein-Barr virus-based episomal vectors in lymphoid cells is approximately 10 to 50 per cell (Yates, et al., 1985). The high copy number of BKV episomes in HT-1376 cells suggests that the steady state level for transcription of genes encoded by such a vector is likely to be very high, and that this vector will be efficiently transferred to the progeny of these bladder transfectants during cellular division. Both of these possibilities were evaluated in the experiments which follow.

C. There is no evidence that pRP-cneoX integrates into HT-1376 genomic DNA. To evaluate if pRP-cneoX also integrates into HT-1376 DNA, total cellular DNA from HT-1376 transfectants was digested with BamHI and evaluated by Southern blot analysis (FIG. 1, Panel B, lane 1). A single band of 9.9 kb, identical in size to BamHI-digested pRP-cneoX plasmid control (lane 2), is consistent with linearized episomal plasmid. Although a 9.9 kb band might also be due to tandem copies of integrated pRP-cneoX plasmid, the absence of other restriction fragments in this analysis indicates that the frequency of integration of the pRP-cneoX episome is very low, beneath the limit of resolution of this assay. This finding is important, since a low frequency of integration of BKV episomes will limit chance insertional activation of proto-oncogenes or insertional inactivation of tumor suppressor genes.

Example 2

The steady state level of transcription of the neomycin resistance gene in pRP-cneoX transfectants is 20-fold higher than in pSV2NEO transfectants. In order to evaluate the potential advantages of utilizing a BKV episomal vector compared to standard plasmid vectors, HT-1376 cells were transacted with pSV2NEO, a plasmid that will be unable to replicate extrachromosomally in HT-1376 cells in the absence of exogenous large T antigen. Following transfection, cells were selected in neomycin, and 5 to 10 clones were combined in each of 3 different pools (a, b, c). Southern analysis of genomic DNA derived from these pools indicated that there were approximately 5 copies of pSV2NEO per cell (data not shown).

To evaluate whether BKV episomal expression vectors can produce high levels of transcription, the steady state level of neomycin resistance gene mRNA from pRP-cneoX and pSV2NEO HT-1376 transfectants were compared by Northern blot analysis. In both plasmids, transcription of the neomycin resistance gene is regulated by the SV40 early promoter.

Northern Blots

Total cellular RNA was prepared by the CsCl isothiocyanate method of Chirgwin, et al. (1979, *Biochem*, 18:5294–5299). Twenty micrograms of total cellular RNA were electrophoresed in 1% agarose formaldehyde gels, transferred to Nytran membranes, hybridized to $^{32}$P-labeled random primed probes, and washed to a final stringency of 0.1xSSC/1.0% SDS at 65° C., as previously described (Cooper, et al., 1990, *Cell Growth Differen.*, 1:149–159).

Figure 2B:

In FIG. 2, Panel A, 20 μg of total cellular RNA from pRP-cneoX (lane 1) and pSV2NEO (pool a, lane 2; pool b, lane 3; pool c, lane 4) transfectants were probed with a radiolabelled BamHI/HindIII fragment of pSV2NEO encoding the neomycin resistance gene. To confirm that approximately equal amounts of mRNA were loaded in each lane, this blot was reprobed with a radiolabelled beta-actin probe (FIG. 2, Panel B).

Densitometric analysis of these data indicates that there are approximately 20-fold higher levels of steady state expression of the neomycin resistance gene in the pRP-cneoX episomal transfectants compared to the pSV2NEO transfectants. This difference is presumably due in part to the higher copy number of pRP-cneoX (150 copies) compared to pSV2NEO (5 copies) in HT-1376 transfectants. These data indicate that BKV episomal expression vectors can achieve substantially higher levels of transcription of a transfected gene than plasmid or retroviral vectors that depend on integration for stable expression.

Example 3

BKV episomal vectors are efficiently transferred to the progeny of bladder transfectants during cellular division. In order to effectively use an episomal expression vector for cDNA library screening, the episome must be efficiently transferred from one transfected cell to its progeny during cell division. A high copy number of episomes per cell may be predictive of efficient vertical transfer since, in this circumstance, it would be unlikely that all episomes would partition to a single daughter cell. Since the parent cell line, HT-1376, clones in soft agar, it was possible to directly evaluate the vertical transfer efficiency of pRP-cneoX in HT-1376 transfectants by plating these cells in soft agar in the presence or absence of neomycin. As a positive control for efficient vertical transfer, pSV2NEO HT-1376 transfectants (pool b), in which the neomycin resistance gene is integrated into HT-1376 DNA, was plated in soft agar in the presence or absence of neomycin.

These results are presented below in Table 1. The parent cell line, HT-1376, clones in soft agar in the absence of neomycin with an efficiency of 0.83%, and does not clone in 200 pg/ml of neomycin, a concentration previously shown to kill these cells after 14 days of incubation. The ratio of soft agar cloning efficiencies with and without neomycin for both types of transfectants is essentially identical, demonstrating efficient transfer of the episome during cell division. In addition, there was no difference in the size of soft agar colonies of HT-1376 pRP-cneoX transfectants grown in the absence or presence of neomycin (data not shown), further evidence in support of efficient vertical transfer of BKV episomes in these cells.

TABLE 1

Vertical transfer efficiency of pRP-cneoX in HT-1376 bladder cells.
SOFT AGAR CLONING EFFICIENCY*

|  | NO NEOMYCIN | 200 μg/ML NEOMYCIN |
| --- | --- | --- |
| ht-1376 | 0.83 +/− 0.09 | 0 |
| ht-1376/pSV2NEO | 0.75 +/− .0.01 | 0.65 +/ 0.16 |
| ht-1376/pRP-cneoX | 0.82 +/− 0.07 | 0.59 +/− 0.17 |

*Cloning efficiency is expressed as the number of soft agar colonies divided by the number of cells plated, tabulated as a percentage. $10^5$ cells were plated per dish and colonies were scored after 3 weeks of growth. Values are the mean of triplicate determinations +/− standard deviation.

Example 4

Figure 3A:
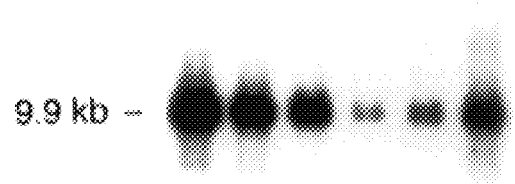
Figure 3B:

BKV episomes persist in bladder transfectants after withdrawal of selection pressure. The high copy number of pRP-cneoX in HT-1376 transfectants and the efficient vertical transfer of this episome to the progeny of these transfectants raised the possibility that pRP-cneoX may be maintained in these cells for several weeks or months without selection pressure. To evaluate the persistence of pRP-cneoX in HT-1376 cells in the absence of selection pressure, these transfectants were grown in complete media without G418, and at various times Hirt supernatant DNA was prepared for Southern analysis. In FIG. 3, lanes 3–6, Hirt supernatant DNA is analyzed from transfectants grown in the absence of G418 for 16, 34, 47, and 64 days, respectively. The sample in lane 2, from cells cultured in the presence of G418 after 122 days of selection, coincides with the 34 day time point during the course of G418 withdrawal, serving as a reference for comparison.

In panel A, this blot was probed with radiolabelled pRP-cneoX. The episome copy number is maintained at essentially unreduced levels following 16 days of withdrawal of G418, and then appears to transiently fall to approximately 10% of the control level by 34 days of selection. Unexpectedly, the episome copy number then increases back to control levels by 64 days of G418 withdrawal.

To evaluate if differences in episomal copy number are due to random inefficiencies in preparation of Hirt supernatant DNA, this blot was rehybridized to a probe for mitochondrial DNA (panel B). The essentially equal amount of mitochondrial DNA in each Hirt supernatant demonstrates that extracts from comparable numbers of cells were loaded in each lane, and that the copy number of pRP-cneoX is indeed maintained at high levels after 64 days of growth in the absence of selection pressure. These data indicate that brief periods of growth of bladder cell transfectants in the absence of G418 will be unlikely to result in loss of episomal plasmid DNA.

Figure 4A:
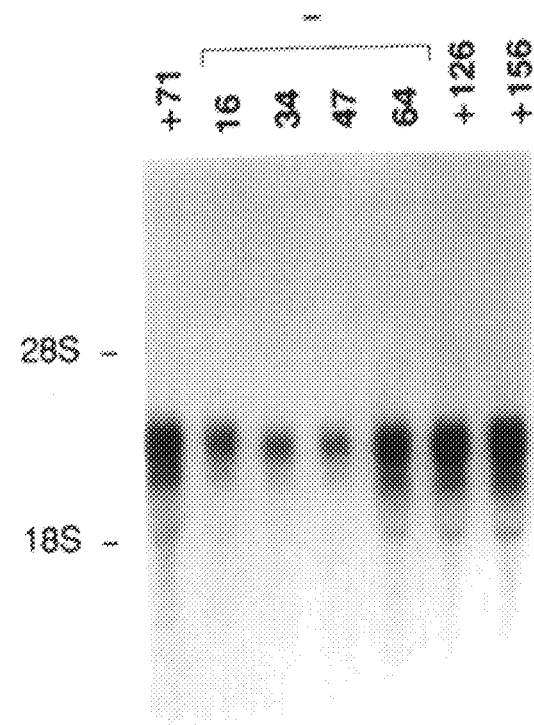
FIGS. 4A and 4B show the persistence of neomycin resistance gene expression in HT-1376 pRP-cneoX transfectants following withdrawal of selection pressure. Northern blot analysis of 20 μg of RNA from HT-1376 transfectants in the presence (71 days, lane 1; 126 days, lane 6; 156 days, lane 7) or absence (16 days, lane 2; 34 days, lane 3; 47 days, lane 4; 64 days, lane 5) of G418. Hybridization probes were a $^{32}$P-labeled BamHI-HindIII fragment of pSV2NEO containing coding sequences of the neomycin resistance gene (A) or $^{32}$P-labeled β-actin plasmid, pHFβA-1 (Gunning, et al., 1983) (B).
Figure 4B:
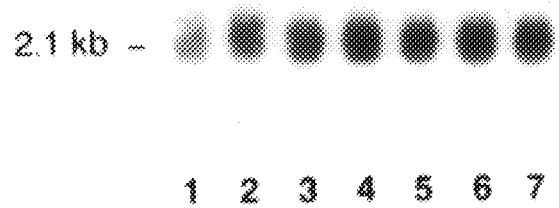

The finding that BKV-derived episomes are maintained at high copy numbers after 2 months of growth in the absence of G418 was unanticipated, since EBV and SV40-derived episomes are usually lost from stable transfectants after 2–4 weeks of growth in the absence of selection pressures (Yates, et al., 1984; Hamber, et al. 1988; Chittenden, et al., 1991). To confirm further that pRP-cneoX is maintained in HT-1376 cells in the absence of G418, we evaluated expression of the neomycin resistance gene during this time course (FIG. 4A). Comparable to the episomal copy number (FIG. 3A), we observed a transient fall in neomycin resistance gene expression followed by return to essentially control levels by 64 days of G418 withdrawal. Equivalent loading of RNA in each lane is demonstrated by rehybridizing this blot with a probe for β-actin (FIG. 4B). These data strongly argue that BKV-derived episomes can be maintained at a high copy number in bladder carcinoma cells in the absence of selection pressure.

Example 5

BKV episomal vectors can be shuttled between HT-1376 bladder cell transfectants and bacteria. An important advantage of episomal expression vectors compared to standard plasmid or viral constructs is the ability to shuttle the episome from stable transfectants into competent bacteria. Hirt supernatant DNA from HT-1376/pRP-cneoX stable transfectants was used to electroporate DH10B *E. coli*. Of 12 minipreps analyzed, 10 had unrearranged episomal plasmid (data not shown), consistent with the findings presented in FIG. 1. For the two colonies having minor rearrangements, it is unclear whether these changes occurred in the bladder cell transfectants or during passage in bacteria.

Example 6

Development of a replication-competent, transformation-negative hybrid SV40/BKV-derived episomal expression system.

The BKV episomal vectors used in Examples 1–5 contained a 3.2 kb fragment of BKV including the origin of DNA replication and the BKV large T antigen (BK-T) transcriptionally regulated by the BKV early promoter. It is expected that BK-T would induce soft agar growth based on its ability to complex wild-type p53 and RB (Mann, et al., 1984; Dyson, et al., 1990). As described below, this vector system was modified by substituting replication-competent, transformation-negative SV40 large T antigen mutants for BK-T. This strategy has been successful, and clones of bladder cell transfectants expressing high levels of SV-T mutant protein remain nontumorigenic and induce plasmids containing SV40 or BKV DNA origins to replicate extrachromosomally.

Wild-type SV-T and each SV-T mutant have been subcloned into the pRc/CMV expression vector (Invitrogen). In this vector, expression of SV-T is regulated by the efficient CMV promoter-enhancer which is active in all bladder cell lines tested. Additionally, lack of down-regulation by SV-T protein makes the CMV promoter-enhancer a good choice for these studies. Wild-type and mutant SV40 large T antigen cDNA were subcloned into the multiple cloning site of the CMV promoter-enhancer transcriptional cassette in the pRC/CMV expression vector (Invitrogen) using a two-part strategy. First, pRC/CMV.T and pRC/CMV. 107-T were constructed. cDNAs encoding wild-type SV40 large T antigen and the 107-T (K1) mutant (Kalderon, et al.) were initially available as subcloned fragments in the unique BamHI site of the pSG5 vector. These vectors were digested with BamHI, fragments containing T antigen cDNA were gel purified, and 3' termini were filled in using the Klenow fragment of DNA polymerase 1. Phosphorylated XbaI linkers were added, followed by XbaI digestion and gel purification. T antigen cDNA clones were then ligated into XbaI-digested, calf intestine alkaline phosphatase-treated pRc/CMV. Orientation of the T antigen cDNA clones was determined by digestion with XmnI and PstI.

Secondly, pRC/CMV.T and pRC/CMV. 107-T were modified to produce pRC/CMV.402-T and pRC/CMV. 107/402-T. A clone of SV40 encoding the codon 402 aspartic acid to glutamic acid mutation in SV40 large T antigen was obtained from the laboratory of Dr. D. Simmons. This clone was digested with HpaI, and a 1067 base pair C-terminal fragment of T antigen was gel purified. Similarly, pRC/CMV.T and pRC/CMV-107-T were digested with HpaI, and the large 6.4 kb fragments were gel purified. The C-terminal HpaI fragment from 402-T was then ligated with calf intestine alkaline phosphatase-treated parent vectors to produce pRC/CMV.402-T and pRC/CMV. 107/402-T. Orientation of the T antigen cDNA clones was determined by digestion with AlwNI.

Figure 5:
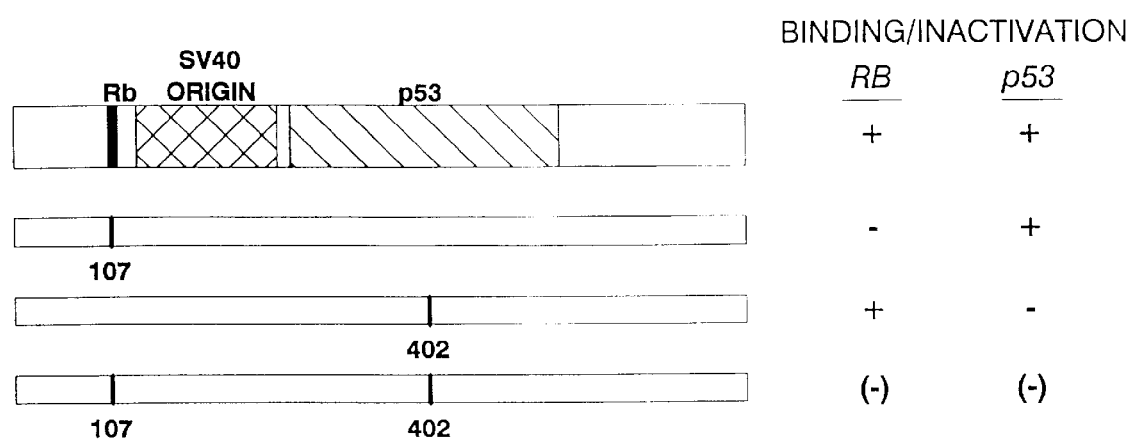
FIG. 5 shows the location of point mutations in replication competent, transformation negative SV40 large T antigen (SV-T) mutants. The p53 and RB binding characteristics of 107/402-T, indicated in parenthesis, are predicted results.

Partial DNA sequence analysis of these constructs confirms that these SV-T mutants do indeed contain the predicted point mutations. FIG. 5 shows the location of point mutations in replication competent, transformation negative SV40 large T antigen (SV-T) mutants. The p53 and RB binding characteristics of 107/402-T, indicated in parenthesis, are predicted results.

Figure 6:
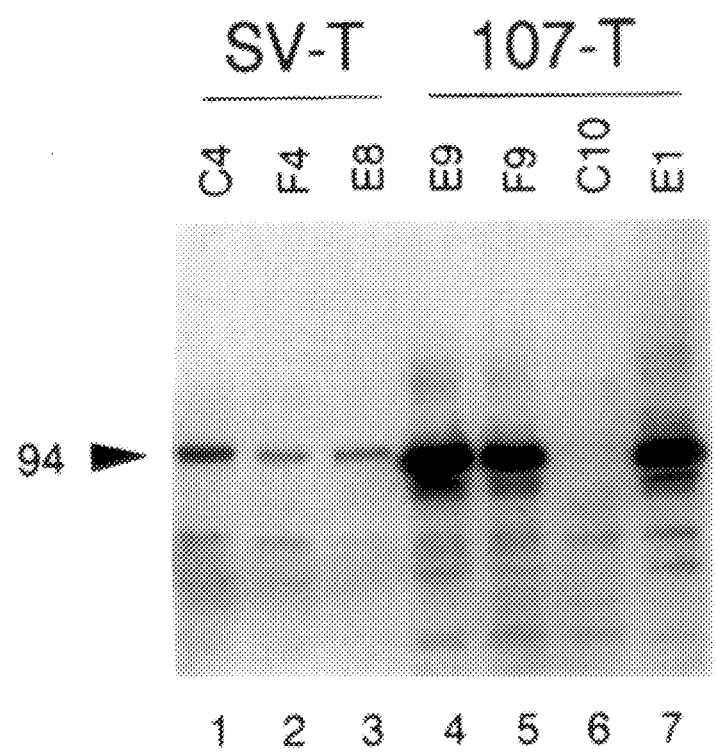
FIG. 6 shows Western blot analysis of single cell clones of 5637 cells stably transfected with SV-T or 107-T. Shown are clones of 5637 cells transfected with pRc/CMV.SV-T (lanes 1–3) or pRc/CMV.107-T (lanes 4–7). Blot was developed using anti-T antigen monoclonal antibody pAB 416 and a chemiluminescent development system (Amersham). 40 μg of lysate were loaded per lane.

A. Expression of large T antigen mutants by nontumorigenic 5637 cell line. Because the 5637 cell line is nontumorigenic and has mutations in both p53 and RB, it seemed likely that expression of either wild-type or mutant SV-T protein would not induce tumorigenic properties. 5637 was therefore chosen for initial transfection studies. 5637 was transfected with pRc/CMV.SV-T and pRc/CMV. 107-T using the lipofection method (Felgner, et al., 1987, *Proc. Natl. Acad. Sci. USA,* 84:7413–7417), stable transfectants were selected in G418, and single cell clones were isolated using cloning cylinders. Shown in FIG. 6 below is a Western blot analysis of representative single cell clones for SV-T and 107-T expression. A protein of 94 kD is detected in these studies, identical in size to T antigen produced in COS-7 control cells. All three SV-T clones have moderate levels of T antigen expression (lanes 1–3). Three out of 4 107-T clones had high levels of T antigen expression (lanes 4, 5, and 7), with clone C10 having no detectable T antigen expression (lane 6). Expression of mutant large T antigen was similarly observed for 5637 cells transfected with pRc/CMV.402-T and pRc/CMV. 107/402-T.

B. Expression of mutant large T antigen does not induce tumorigenic properties in susceptible cells. Clones of SV-T and 107-T 5637 transfectants have been evaluated for the ability to grow in soft agar, to form foci in tissue culture, and to form tumors in the flanks of nude mice. Three 5637 clones were chosen for these initial studies (see FIG. 6): C4 (SV-T expressor); C10 (107-T non-expresser); and E1 (107-T expresser).

Soft Agar Cloning

Transformed cells were trypsinized and then passed through a 30-micron nylon filter (Tetko, Lancaster, N.Y.) to achieve a single cell suspension. The bottom layer of agar consisted of low glucose DMEM supplemented with 10% fetal calf serum and 0.6% Seaplaque agarose (FMC BioProducts, Rockland, ME). The top layer contained serial dilutions of cells ranging between $10^3$ and $10^6$ in low-glucose DMEM supplemented with 10% fetal calf serum and 0.3% Seaplaque agarose. Aggregates of cells greater than 125 $\mu$m in diameter (~50 cells) were scored as colonies, and dishes were observed for at least 1 month after plating. These data are summarize below in Table 2.

The parent nontumorigenic 5637 cell line does not clone in soft agar, form foci in tissue culture, and only 1/12 nude mice inoculated formed a tumor after a prolonged latency period. The moderate SV-T expressor, C4, remains nontumorigenic in nude mice and does not clone in soft agar. Interestingly, this clone forms microscopic foci, although does not form macroscopic foci. As expected, clone C10, the 107-T non-expresser, is nontumorigenic with an identical profile as the parental 5637 cell line. The high level 107-T expresser, E1, has an identical profile as C4, with formation of microscopic foci, but no growth in soft agar or in nude mice. These data demonstrate that we have successfully expressed T antigen protein in nontumorigenic bladder carcinoma cells without inducing anchorage independence or tumor formation in nude mice.

TABLE 2

5637 bladder carcinoma cells transfected with wild-type (SV-T) or mutant (107-T) SV40 large T antigens remain nontumorigenic.

|  | T ANTIGEN | FOCUS | SA (%) | TUMORS | LATENCY (WKS) |
|---|---|---|---|---|---|
| Parental | − | − | 0 | 1/12 | 12 |
| SV-T C4 | + | +/− | 0 | 0/6 | — |
| 107-T C10 | − | − | 0 | 0/6 | — |
| 107-T E1 | ++ | +/− | 0 | 0/6 | — |

T ANTIGEN, level of T antigen expression (− none, + moderate, ++ high); FOCUS, focus formation (− none, +/− microscopic foci); SA, soft agar growth; TUMORS, # tumors/total number of nude mice inoculated; LATENCY, time (weeks) to achieve tumor volume > 250 mm$^3$ Expression of wild-type SV40 T antigen will confer soft agar growth in a suitable recipient cell line. Since T24 cell line has wild-type RB (and mutant p53), expression of SV-T or 402-T is expected to inactivate RB protein. We have characterized tumorigenic properties in clones of T24 cells expressing moderate levels of SV-T (A7) and 402-T (G1). Whereas the parent T 24 cell line does not clone in soft agar, A7 and G1 have cloning efficiencies of 0.10%±0.02% (se) and 0.12% ±0.04%, respectively. These findings indicate that the T antigen proteins expressed in these transfectants are biologically functional molecules retaining transformation properties. In contrast, a single cell clone of T24 expressing high levels of 107/402-T does not grow in soft agar.

Figure 7:
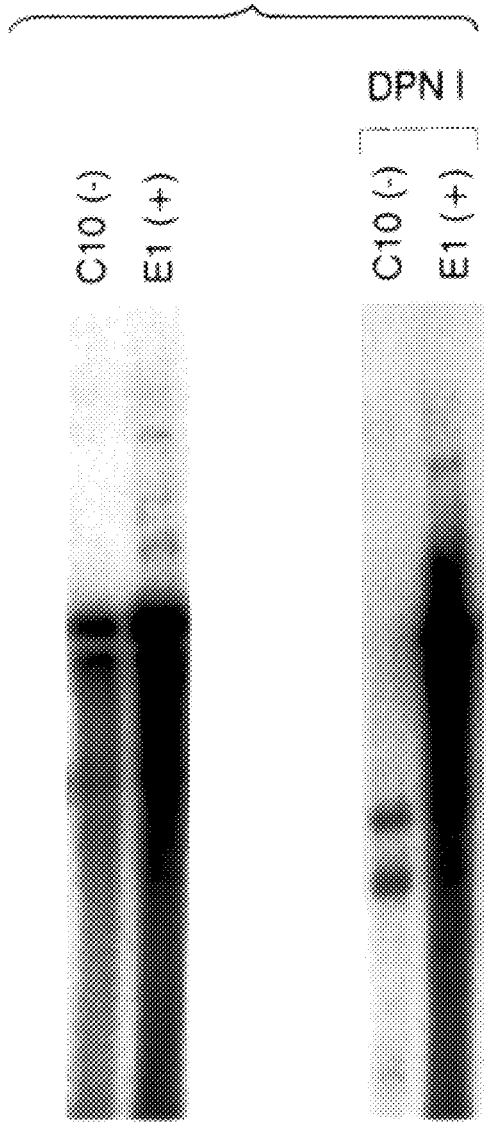
FIG. 7. Southern blot analysis demonstrating that 107-T drives extrachromosomal replication of a plasmid (pSV2CAT containing the SV40 origin of DNA replication. 107-T 5637 clones C10 (no detectable expression) and E1 (high level expression) were transfected with pSV2CAT, and Hirt supernatant DNA was prepared approximately 4 days after transfection. Hirt supernatant DNA from approximately $5 \times 10^5$ cells was loaded per lane, and evaluated before and after digested by DpnI, as indicated above. Hybridization probe was $^{32}$P-labelled pSV2CAT.

C. 107-T can drive replication of the SV40 DNA origin. A biological function expected for SV-T and 107-T is the ability to drive replication of the SV40 DNA origin. To evaluate replication activity of 107-T, 5637 clones C10 and E1 were transfected with pSV2CAT, a plasmid containing the SV40 DNA origin. Four days after transfection, Hirt supernatant DNA was prepared and evaluated for evidence of episomal replication, as illustrated in FIG. 7.

Extrachromosomal replication can be assayed by determining if Hirt supernatant DNA is partially resistant to digestion by DpnI. Whereas plasmid DNA prepared in DNA adenine methylase positive bacteria are methylated at adenine nucleotides at the sequence GATC, mammalian cells lack this enzyme, and hence human DNA is resistant to digestion by DpnI. As observed in FIG. 7, Hirt DNA prepared from the C10 5637 clone (107-T non-expresser) fails to support episomal replication, since pSV2CAT is efficiently digested by DpnI. In contrast, Hirt DNA prepared from the E1 5637 clone (107-T expresser) is largely resistant to digestion by DpnI, indicating that pSV2CAT is replicating extrachromosomally in these transfectants. These data demonstrate that SV40 large T antigens expressed in bladder cell transfectants are biologically functional molecules, possessing replication activity.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

I claim:

1. A method for identifying a candidate oncogene, comprising the steps of:
   introducing episomes into non-tumorigenic cells, each of said episomes comprising:
   (a) a replication competent, transformation negative vector comprising at least one papovavirus origin of replication and a first DNA sequence encoding a papovavirus large T antigen which contains a replication competent binding site for said origin of replication and which is negative for binding to both wild-type p53 tumor suppressor and retinoblastoma tumor suppressor, said first DNA sequence being operatively linked to a first promoter which is functional in said non-tumorigenic cells; and
   (b) a second DNA sequence operatively linked to a second promoter which is functional in the non-tumorigenic cells, wherein the second DNA sequence is a cDNA which is complementary to mRNA obtained from tumorigenic cells; and
   screening the resulting cells for a tumorigenic phenotype, wherein the resulting cells which display said tumorigenic phenotype contain a CDNA comprising said candidate oncogene.

2. A method for identifying a candidate anti-oncogene, comprising the steps of:
   introducing episomes into non-tumorigenic cells, each of said episomes comprising:
   (a) a replication competent, transformation negative vector comprising at least one papovavirus origin of replication and a first DNA sequence encoding a papovavirus large T antigen which contains a replication competent binding site for said origin of replication and which is negative for binding to both wild-type p53 tumor suppressor and retinoblastoma tumor suppressor, said first DNA sequence being operatively linked to a first promoter which is functional in said non-tumorigenic cells; and (b) a second DNA sequence operatively linked in an anti-sense orientation to a second promoter which is functional in the non-tumorigenic cells, wherein the second DNA sequence is a cDNA which is complementary to mRNA obtained from non-tumorigenic, anchorage-dependent cells; and screening the resulting cells for a tumorigenic phenotype, wherein the resulting cells which display said tumorigenic phenotype contain in an antisense orientation a cDNA comprising said candidate anti-oncogene.

* * * * *